United States Patent
Bastia

(10) Patent No.: US 10,349,850 B2
(45) Date of Patent: Jul. 16, 2019

(54) MANOMETRIC PROBE

(71) Applicant: THD S.P.A., Correggio (Reggio Emilia) (IT)

(72) Inventor: Filippo Bastia, Soliera (IT)

(73) Assignee: THD S.P.A., Correggio (IT)

( * ) Notice: Subject to any disclaimer, the term of this patent is extended or adjusted under 35 U.S.C. 154(b) by 389 days.

(21) Appl. No.: 15/156,527

(22) Filed: May 17, 2016

(65) Prior Publication Data

US 2016/0338606 A1    Nov. 24, 2016

(30) Foreign Application Priority Data

May 20, 2015    (IT) .................... 102015000016047

(51) Int. Cl.
| | | |
|---|---|---|
| *A61B 5/00* | (2006.01) | |
| *A61B 5/03* | (2006.01) | |
| *A61B 5/22* | (2006.01) | |
| *A61B 5/11* | (2006.01) | |

(52) U.S. Cl.
CPC .............. *A61B 5/036* (2013.01); *A61B 5/1107* (2013.01); *A61B 5/227* (2013.01); *A61B 5/4255* (2013.01); *A61B 2560/0425* (2013.01); *A61B 2562/168* (2013.01)

(58) Field of Classification Search
CPC ....... A61B 5/1107; A61B 5/227; A61B 5/225; A61B 5/036; A61B 5/4255
USPC ......................................................... 600/593
See application file for complete search history.

(56) References Cited

U.S. PATENT DOCUMENTS

| | | | |
|---|---|---|---|
| 4,776,347 A | 10/1988 | Matthews | |
| 8,845,545 B2 * | 9/2014 | Folkerts ............. | A61B 5/04882 600/557 |
| 2006/0036188 A1 | 2/2006 | Hoffman et al. | |
| 2007/0112284 A1 | 5/2007 | Hoffman et al. | |
| 2010/0087757 A1 | 4/2010 | Hoffman et al. | |

FOREIGN PATENT DOCUMENTS

| | | |
|---|---|---|
| GB | 1532360 A | 11/1978 |
| JP | 2002143133 A | 5/2002 |

\* cited by examiner

*Primary Examiner* — Max F Hindenburg
(74) *Attorney, Agent, or Firm* — Pearne & Gordon LLP

(57) ABSTRACT

A manometric probe, comprising:
a main body (2) provided with a longitudinal axis (X);
an extensible membrane (3) sealingly associated to at least two annular areas of the main body (2) so as to delimit a chamber (4) external to the main body (2);
feed means (51,52) arranged so as to enable feeding of a fluid inside the chamber (4).

15 Claims, 4 Drawing Sheets

MANOMETRIC PROBE

The invention has for object a manometric probe destined to the manometry test.

In the present description and the appended claims, the terms "proximal" and "distal" refer to the operator using the probe. In particular, by the term "proximal" it is meant a portion, one end or more, generally an element positioned near the operator who is using the probe, whereas by the term "distal" it is meant a portion, one end or more, generally an element positioned away from the operator who is using the probe.

For clinical assessment of the state of health of the anal sphincter, several tests are currently effected, which include a manometric measurement, in order to assess ability of the sphincter muscles to exert sufficient closing pressure for retaining solids, liquids and gases.

The manometric measurement is carried out via probes or catheters to be introduced into the sphincters. These probes comprise a tubular body provided with a balloon disposed at a distal end. The tubular body is inserted into the anal canal such that the balloon enters the rectum ampulla, thus acting as an anchoring element of the probe.

In the tubular body portion concerned to the tract of the sphincters, there are present holes to which a pressurized fluid is generally fed via channels located internally of the tubular body, so that the tone of the sphincter muscles themselves can be measured.

Depending on the fluid that is used, the methods of measurements may be different.

In the case where a pressurized fluid is fed, the fluid comes out from the holes in the tubular body and interacts directly with the walls of the anal canal. In this case one proceeds with measuring the resistance opposed by the walls of the anal canal to the fluid spill.

Alternatively the holes are associated with balloons fed with a gas. In this case one proceeds with punctual measurement (at the balloon) of the resistance opposed by the walls of the anal canal to the expansion of the balloon.

Alternatively piezometric probes are used that in the field are termed probes in the solid state, which piezometric probes, once in contact with the anal canal perform the measurements.

The probes and measurement methods currently used exhibit numerous drawbacks.

First of all, such instruments and examinations are extremely troublesome for patients. The examination requires a relatively long time indeed, and the manner of performance are quite invasive.

The examinations realized with the techniques briefly described above, provide precise numerical values i.e. in connection to some points located in the channel tract of difficult interpretation.

Furthermore, the pressure values detected are significant only with respect to a specific probe calibration value. The results obtained depend therefore both on how the calibration is carried out, which requires a certain expertise on the part of the physician, and on the type of apparatus used, which introduces its own and diversified load losses between an apparatus and the other. This implies that the results obtained are not of the absolute type, thus the results obtained may not be used for comparison with the data obtained from different apparatuses and/or operators, i.e. such data are not usable at the scientific level.

It is an object of the present invention to provide a manometric probe which allows to overcome the drawbacks of the currently available devices.

An advantage of the probe according to the present invention is that it allows to obtain substantially absolute data, i.e. standardized and shareable data.

A further advantage of the probe according to the present invention is to allow a considerable reduction of the time required to conduct the examination while reducing invasiveness and increasing comfort for the patient.

Further characteristics and advantages of the present invention will better emerge from the detailed description that follows of a preferred embodiment of the invention herein disclosed, illustrated by way of non-limiting example in the appended figures wherein.

Figure 1:
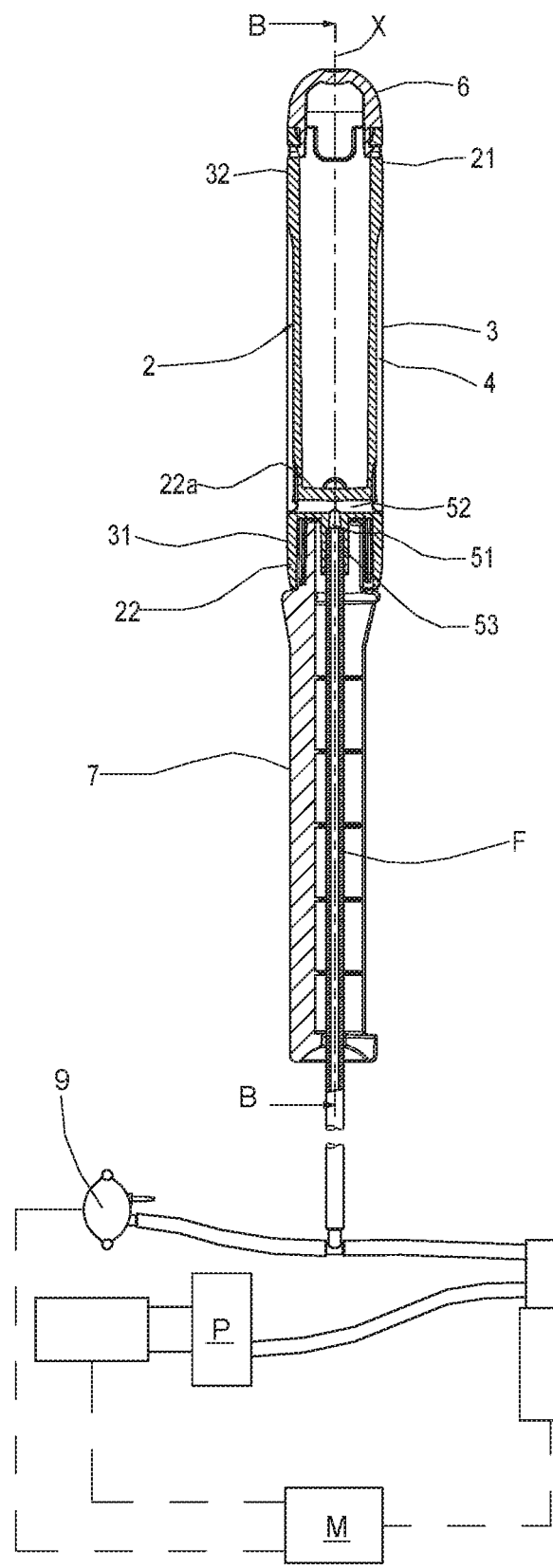
FIG. 1 shows a first view of the probe according to the present invention, taken along the sectional plane A-A of FIG. 2.

The manometric probe according to the present invention comprises a main body (2) provided with a longitudinal axis (X). Preferably, the main body (2) exhibits a cylindrical shape which is concentric to the longitudinal axis (X). Furthermore, the main body (2) is preferably hollow.

The main body (2) comprises a distal end (21) preferably intended to be introduced into the anal canal. Such distal end (21) is closed by a rounded-shaped plug (6). The plug (6) may be associated to the main body (2) with snap-engagement, possibly of the detachable type, so that removal of the plug (6) is allowed.

The main body (2) further comprises a proximal end (22) to which there is associated an handgrip (7). Connection between the handgrip (7) and the main body (2) can be realized for example by snap-fittings. In the embodiment illustrated there are provided two snap-fittings (7a) opposite to one another on the outer surface of the main body (2) and two internal snap-fittings (7b) formed between a pair of tabs integral with the handgrip (7) and a pair of seats afforded in the proximal end (22) and intended to receive the tabs of the handgrip (7).

The manometric probe further comprises an extensible membrane (3), which is sealingly associated with at least two annular zones of the main body (2) so that a chamber (4) is defined, which is external to the main body (2). The chamber (4) may be fed with a pressurized fluid.

The extensible membrane (3) exhibits a substantially tubular shape and is arranged concentrically to the main body (2), outside the main body itself. The two end edges (31,32) of the extensible membrane are sealingly joined to the outer surface of the main body (2). The sealing conjunction between the end edges (31,32) of the membrane (3) and the outer surface of the main body (2) is obtained preferably by heat sealing. Alternatively, the conjunction may be obtained by bonding.

In addition, the sealing conjunction between the end edges (31,32) of the membrane (3) and the outer surface of the main body (2) extends along a stretch of a pre-determined length (in the longitudinal axis direction (X) of the outer surface of the main body (2). In other words, between the membrane (3) and the outer surface of the main body (2), disposed in the vicinity of the end edges (31,32), two annular junction bands (31a, 32a) are defined. In this way the risk is reduced of any leakage substantially along the end edges (31,32) of the membrane (3).

Preferably, the outer surface of the main body (2), in the area facing the extensible membrane (3), exhibits a narrowing (20), or a reduction of the outer diameter, so that a recess is formed, which helps to delimit the chamber (4). The narrowing (20) increases the volume of the chamber (4) compared to a solution in which the outer surface of the main body (2) exhibits a constant external diameter, so that the filling of the chamber by means of a fluid may takes place in a more gradual and uniform manner. The narrowing (20) also has the advantage of generating a flow-path that allows the fluid to enter the chamber (4), by exerting a pressure on the membrane (3) also in case of external pressure acting on the membrane (3) itself.

Figure 2:
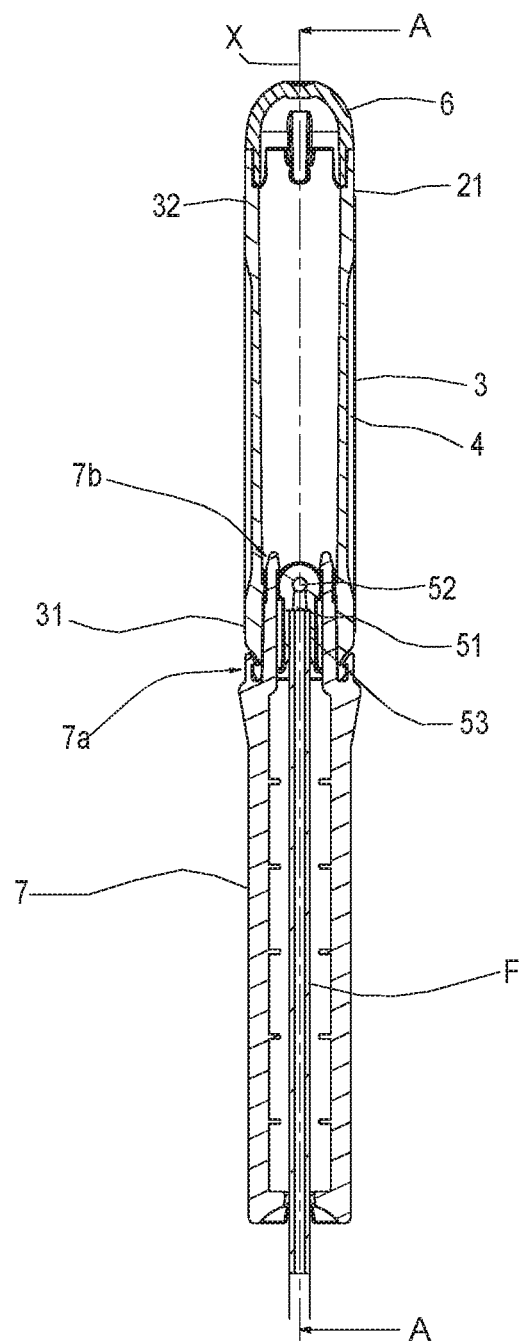
FIG. 2 shows a second sectional view of the probe according to the present invention, taken along the sectional plane B-B of FIG. 1.
Figure 3:
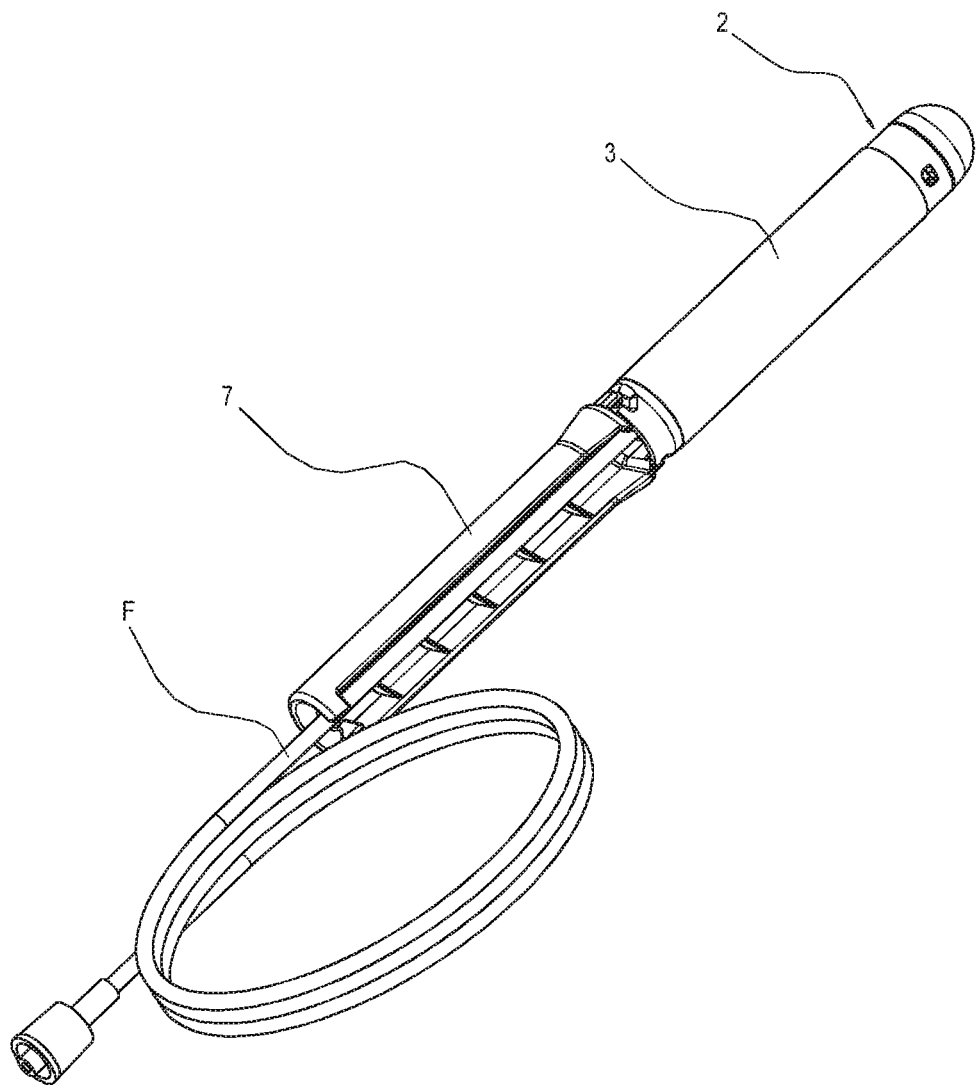
FIG. 3 shows an isometric view of the probe according to the present invention.
Figure 4:
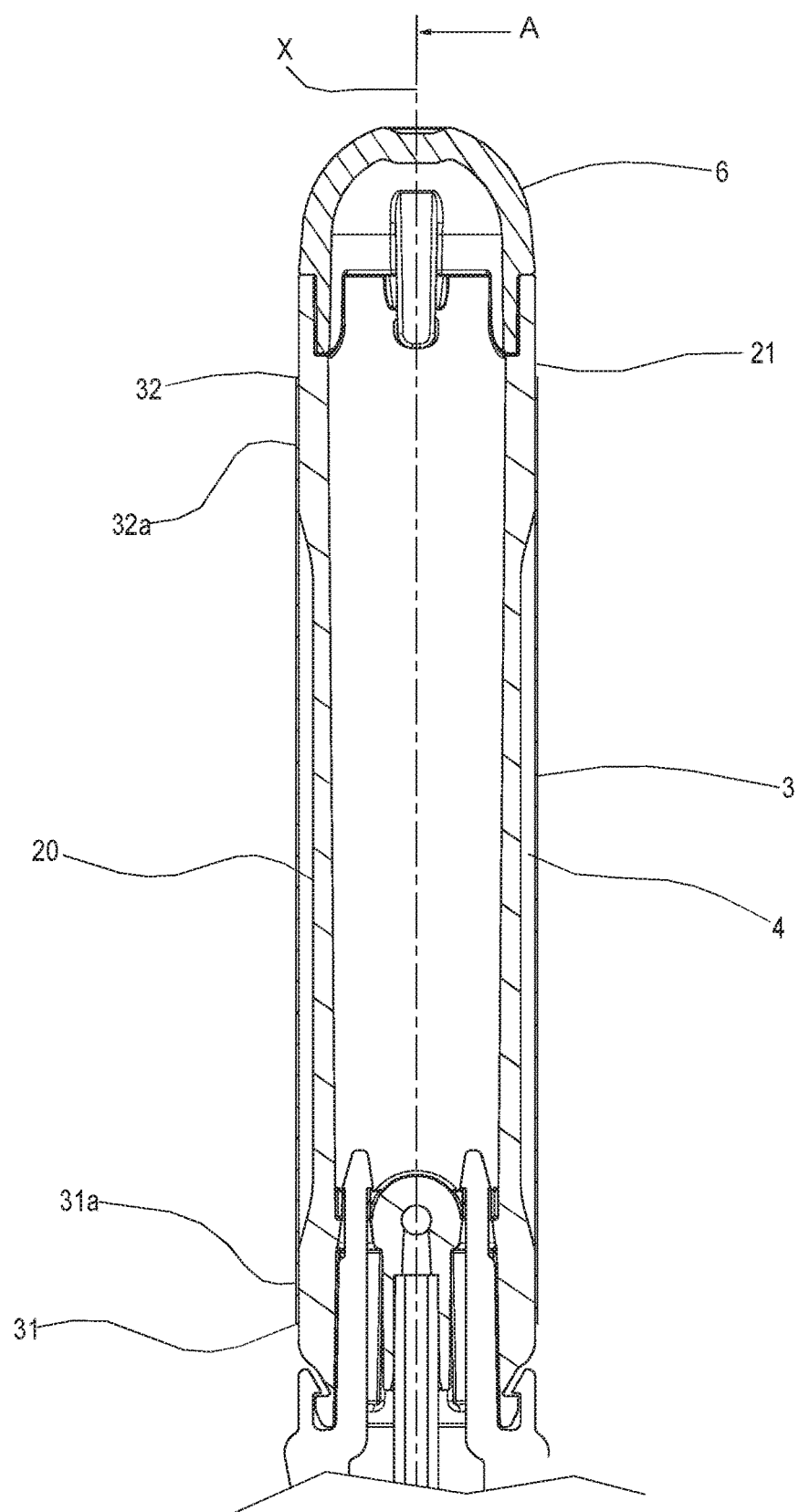
FIG. 4 shows an area of the probe illustrated in FIG. 2 on enlarged scale.

With particular reference to FIG. 2, the chamber (4) thus extends outwards of the main body (2), between the end edges (31,32). If the narrowing (20) is present, the extensible membrane (3) remains spaced from the outer surface of the main body (2), at least in the narrowing area (20). The annular junction bands (31a, 32a) are located at the ends of the narrowing (20), outside of the latter, i.e. the annular junction bands (31a, 32a) are located on areas of the main body (2) not affected by the narrowing (20).

Due to extensibility of the membrane (3), the volume in the chamber (4) may vary according to the volume of fluid that is introduced therein. The membrane (3) may assume at least one relaxed configuration, corresponding to a condition in which the chamber (4) is in communication with an external environment and/or is not filled with fluid, and at least one extended configuration, corresponding to a condition wherein the chamber (4) is filled with a pre-determined volume of fluid at a given pressure. In the extended configuration the extensible membrane (3) is detached and kept separate from the outer surface of the main body (2) by the pressure of the fluid present in the chamber (4). In these conditions, a reduction of the volume in the chamber (4) obtained for example by exerting pressure on the extensible membrane (3), determines a pressure increase in the chamber (4). The measurement of the pressure in the chamber (4) is therefore essentially equivalent to the measurement of the pressure exerted from the outside on the extensible membrane (3).

Feed means (51,52) is arranged to allow sending of a fluid inside the chamber (4).

These feed means comprises a first conduit (51), arranged to be associated with a source of pressurized fluid, the conduit (51) being placed in communication with the chamber (4). In the illustrated embodiment, the first conduit (51) is formed through the main body (2).

In particular the first conduit (51) is disposed through a fitting (53) parallel or coaxial to the longitudinal axis (X). Such fitting (53) is positioned at the proximal end (22) of the main body (2). The fitting (53) is configured to allow tight connection of a further feed conduit (F) coming from the source of pressurized fluid, such as a pump or a compressor. This additional feed conduit, not shown, is disposed internally of the handgrip (7).

Preferably the feed means comprises at least a second conduit (52). This second conduit (52) is arranged transversely to the first conduit (51). In particular, the second conduit (52) is branching off transversely to a distal end of the first conduit (51) and, at the ends thereof, it is opening into the chamber (4). In other words, the first and second conduit (51,52) define a single, preferably T-shaped conduit provided with an inlet end, at which inlet end the single T-shaped conduit may be connected to a pressurized fluid source, the single T-shaped conduit being further provided with two outlet ends flowing inside the chamber (4).

In the illustrated embodiment, the main body (2) comprises a transverse partition (22a) disposed in the proximal end area (22). Such transverse partition (22a) is arranged perpendicularly to the longitudinal axis (X). The second conduit (52) is formed through the transverse partition (22a). The fitting (53), via which the first conduit (51) is obtained, is integral with the transverse partition (22a). The first conduit (51) is flowing into the second conduit (52).

The manometric probe according to the present invention can be used in a device for measuring the encircling pressure exerted by the walls of a conduit, for example the anal sphincter. The device, in addition to the probe itself, comprises a pressure gauge (9), which is predisposed for measuring the pressure in the chamber (4). The pressure gauge (9) was illustrated only schematically since already known to the men skilled in the art.

The device further comprises a source of pressurized fluid (P), e.g. a pump or a compressor connected to the feed means (51,52). As already mentioned, the connection between the source (P) and the feed means (51,52) can be done via a conduit (F) housed internally of the handgrip (7).

The device is further provided with a control module (M), arranged to receive as input the values of pressure sensed by the pressure gauge (9) and to process these values into corresponding output data.

The measurement of the encircling pressure performed by means of the probe according to the invention occurs in the following way.

The chamber (4) is filled with fluid at a pre-determined and known pressure, e.g. about 150 mmHg, so that the extensible membrane (3) is inflated. This pre-determined pressure is essentially a reference pressure (with zero value) with respect to which the pressure that is being investigated, is measured. Without prejudice to any altimetric variations, of which it is fairly easy to take account, the pressure measured relative to the reference pressure or zero value, is a pressure that, from a practical point of view, is substantially an absolute value and comparable with other pressures sensed in the same manner.

Following inflation of the extensible membrane (3), the probe may be inserted into the conduit of which one wishes to measure the pressure exerted by the walls. The pressure exerted by the walls of the conduit produces a variation in the volume of the chamber (4) and a corresponding pressure variation in the chamber (4) which, under equilibrium conditions, equals the pressure exerted by the walls of the conduit. Such pressure is sensed by the pressure gauge (9) and sent to the control module (M) which provides to process the differential pressure value with respect to the reference pressure.

In the case of a measurement relative to the anal sphincter, after inflating the extensible membrane (3) at a pre-determined pressure, the probe is inserted into the sphincter itself and positioned so that the area within the end edges (31,32) of the membrane (3) is within the anal conduit.

Following positioning of the probe, the desired measurements may be performed. For example it is possible to detect the pressure with the sphincter in its rest conditions and/or during the various steps of control of the sphincter by the patient, for example during a squeeze step (i.e. a step of retention contraction), the duration of which step may be also detected, and during a step in which the Valsalva maneuver is performed by the patient.

The different pressure levels are acquired by the control module, which provides to process and exhibit the output data.

The probe according to the present invention offers important advantages. Firstly, it deals with a device exhibiting a very simple structure, and which may be therefore realized in a much more accurate and repeatable manner than the devices of the prior art. Additionally, the presence of the extensible membrane does not particularly bother the patient, who is not subject to the effects arising from jets of liquids or gases, unlike currently available probes. In other words, apart from the unavoidable presence of the main body (2), the patient is not forced to undergo the effect generated by additional interaction and/or measurement means. A further advantage offered by the probe is that the pressure measured by means of the extensible membrane (3) is an average or overall pressure that is exerted by the anal sphincter, and not a series of punctual or very localized values as is the case of currently available probes. It deals in essence with a pressure value which is simple, clear and of immediate practical benefit, thanks to which presence of any disease or dysfunction may be promptly recognized.

The invention claimed is:

1. A manometric probe, comprising:
a main body (2), provided with a longitudinal axis (X);
an extensible membrane (3), associated to an outer surface of the main body (2) so as to delimit a chamber (4) external to the main body (2);
feeding means (51, 52) arranged to allow feeding of a fluid into the chamber (4); characterized in that:
the membrane (3) is sealingly connected to the outer surface of the main body (2) in at least two annular junction areas (31a, 32a), at least one of the annular junction areas extending parallel to the longitudinal axis (X);
the main body (2) exhibits a narrowing (20), which extends between the two annular junction areas (31a, 32a).

2. A probe according to claim 1, wherein the annular junction areas (31a, 32a) comprise two end edges (31, 32) of the membrane (3).

3. A probe according to claim 1, wherein the feeding means comprises a first conduit (51), which is arranged to be associated with a source of pressurized fluid and placed in communication with the chamber (4).

4. A probe according to claim 3, wherein the first conduit (51) is formed through the main body (2); the feeding means comprises at least a second conduit (52) which, at the ends thereof, opens into the chamber (4) and is arranged transversely to the first conduit (51).

5. A probe according to claim 3, wherein the first conduit (51) is disposed through a fitting (53) parallel or coaxial to the longitudinal axis (X).

6. A probe according to claim 5, wherein: the main body (2) comprises a transverse partition (22a) disposed in the proximal end area (22) perpendicularly to the longitudinal axis (X); the second conduit (52) is formed through the transverse partition (22a).

7. A probe according to claim 6, wherein: the main body (2) comprises a fitting (53), associated with the transverse partition (22a); the first conduit (51) is formed through the fitting (53).

8. A probe according to claim 1, wherein the main body (2) is hollow.

9. A probe according to claim 1, wherein the main body (2), at a distal end (21) thereof, is closed by a plug (6).

10. A probe according to claim 1, further comprising a handgrip (7) associated to a proximal end (22) of the main body (2).

11. A device for measuring the narrowing pressure exerted by the walls of a conduit, in particular an anal sphincter, comprising:
a manometric probe (1) according to claim 1;
a pressure gauge (9), arranged to measure the pressure in the chamber (4);
a source of pressurized fluid connected to the feed means (51,52);
a control module, arranged for receiving in input the pressure values detected by the pressure gauge (9) and for processing said values into corresponding output data.

12. A method for measuring the narrowing pressure exerted by the walls of a conduit, comprising the following steps:
providing a device according to claim 11,
feeding a certain volume of fluid to the chamber (4) of the device until a preset reference pressure is reached;
inserting the main body (2) into the conduit;
detecting the variation in pressure inside the chamber (4) with respect to the reference pressure by means of the pressure gauge (9).

13. The probe according to claim 1, wherein both of said at least two annular junction areas extend parallel to the longitudinal axis (X).

14. The probe according to claim 1, wherein the membrane (3) is sealingly connected via heat sealing or bonding to the outer surface of the main body (2) in the at least one annular junction area extending parallel to the longitudinal axis (X).

15. The probe according to claim 13, wherein the membrane (3) is sealingly connected via heat sealing or bonding to the outer surface of the main body (2) in both of the at least two annular junction areas.

* * * * *